United States Patent
Adams et al.

(10) Patent No.: US 10,258,753 B2
(45) Date of Patent: Apr. 16, 2019

(54) SYSTEM, METHOD, USE AND INFORMATION STORAGE MEDIUM FOR PRACTICING OF AN INHALATION PROCESS

(71) Applicant: Boehringer Ingelheim International GmbH, Ingelheim am Rhein (DE)

(72) Inventors: Patricia Adams, Ingelheim am Rhein (DE); Marion Frank, Ingelheim am Rhein (DE); Herbert Wachtel, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 745 days.

(21) Appl. No.: 14/044,169

(22) Filed: Oct. 2, 2013

(65) Prior Publication Data
US 2014/0106324 A1   Apr. 17, 2014

(30) Foreign Application Priority Data

Oct. 4, 2012   (EP) .................................. 12 006 897
Oct. 22, 2012  (EP) .................................. 12 007 259

(51) Int. Cl.
  *G09B 23/28*   (2006.01)
  *A61M 15/00*   (2006.01)
  (Continued)

(52) U.S. Cl.
  CPC .......... *A61M 15/009* (2013.01); *A61B 5/087* (2013.01); *A61B 5/6898* (2013.01);
  (Continued)

(58) Field of Classification Search
  CPC ...................................................... G09B 23/28
  See application file for complete search history.

(56) References Cited

U.S. PATENT DOCUMENTS 5,333,106 A   7/1994   Lanpher et al.
5,363,842 A   11/1994  Mishelevich et al.
(Continued)

FOREIGN PATENT DOCUMENTS

DE   20 2008 010 475 U1   3/2009
DE   20 2011 106 292 U1   2/2012
(Continued)

OTHER PUBLICATIONS

Josh Wolford, Spirosmart App Trns Your Iphone into an Accuragte Spirometer, Webrpnews, Found on the Internet Jun. 25, 2003; www.webpronews.com/spirosmart-app-turns-your-iphone-into-an-accurate-spirometer-2012-09-; *The Whole Document*.

(Continued)

*Primary Examiner* — Sam Yao
*Assistant Examiner* — Evan Page
(74) *Attorney, Agent, or Firm* — David S. Safran; Roberts Mlotkowski Safran Cole & Calderon, P.C.

(57) ABSTRACT

An inhalation training system and a method for practicing of an inhalation process and a method of operating a portable communications device in this respect and to an information storage medium are improved. An air flow during inhalation is converted into an acoustic signal, especially a whistling tone. The acoustic signal is picked up by a microphone of a portable communications device, such as a smartphone, and is electronically evaluated. The inhalation training system has a mouthpiece and a converter apparatus for converting the air flow into the acoustic signal and in addition has a holding apparatus for especially detachable holding of the communications device.

5 Claims, 7 Drawing Sheets

(51) Int. Cl.
*G09B 9/00* (2006.01)
*A61B 5/00* (2006.01)
*A61B 5/087* (2006.01)
*H04M 1/21* (2006.01)
*A63B 23/18* (2006.01)

(52) U.S. Cl.
CPC ........... *A61B 5/7415* (2013.01); *A61M 15/00* (2013.01); *G09B 9/00* (2013.01); *A61B 5/742* (2013.01); *A61M 2202/064* (2013.01); *A61M 2205/056* (2013.01); *A61M 2205/3375* (2013.01); *A61M 2205/3569* (2013.01); *A61M 2205/3584* (2013.01); *A61M 2205/43* (2013.01); *A61M 2205/502* (2013.01); *A61M 2205/581* (2013.01); *A61M 2205/583* (2013.01); *A63B 23/185* (2013.01); *A63B 2225/50* (2013.01); *A63B 2230/40* (2013.01); *H04M 1/21* (2013.01)

(56) References Cited

U.S. PATENT DOCUMENTS

| | | | |
|---|---|---|---|
| 5,839,429 | A | 11/1998 | Marnfeldt et al. |
| 6,116,233 | A | 9/2000 | Denyer et al. |
| 6,597,793 | B1 | 7/2003 | Darbut et al. |
| 2003/0041859 | A1 | 3/2003 | Abrams et al. |
| 2004/0187869 | A1 | 9/2004 | Bjorndal et al. |
| 2005/0247305 | A1* | 11/2005 | Zierenberg ........ A61M 15/0065 128/200.14 |
| 2009/0263773 | A1 | 10/2009 | Kotlyar et al. |
| 2010/0192948 | A1 | 8/2010 | Sutherland et al. |
| 2011/0226236 | A1 | 9/2011 | Buchberger |
| 2011/0226242 | A1* | 9/2011 | Von Hollen ........ A61M 15/009 128/203.12 |
| 2012/0116241 | A1 | 5/2012 | Shieh et al. |
| 2012/0247235 | A1 | 10/2012 | Adamo et al. |
| 2013/0008436 | A1 | 1/2013 | Von Hollen et al. |
| 2013/0190641 | A1* | 7/2013 | Gonnen ............... A61B 5/0002 600/538 |
| 2013/0206136 | A1 | 8/2013 | Herrmann et al. |
| 2014/0106324 | A1 | 4/2014 | Adams et al. |

FOREIGN PATENT DOCUMENTS

| | | |
|---|---|---|
| EP | 0 667 168 A1 | 8/1995 |
| EP | 0 933 092 A1 | 8/1999 |
| GB | 2479953 A | 11/2011 |
| JP | 2012-110499 A | 6/2012 |
| WO | 95/26212 A1 | 10/1995 |
| WO | 97/13553 A1 | 4/1997 |
| WO | 99/38556 A1 | 8/1999 |
| WO | 00/69496 A1 | 11/2000 |
| WO | 2006/008745 A2 | 1/2006 |
| WO | 2007/101438 A1 | 9/2007 |
| WO | 2010/023591 A2 | 3/2010 |
| WO | 2011/056889 A1 | 5/2011 |
| WO | 2011/083377 A1 | 7/2011 |
| WO | 2011/135353 A1 | 11/2011 |
| WO | 2011/153406 A2 | 12/2011 |
| WO | 2012/038903 A2 | 3/2012 |
| WO | 2013/020591 A1 | 2/2013 |

OTHER PUBLICATIONS

Josh Wolford, Spirosmart App Turns Your Iphone Into an Accurage Spirometer, Internet Citation, Sep. 20, 2012, pp. 1-2,The Whole Document.

* cited by examiner

SYSTEM, METHOD, USE AND INFORMATION STORAGE MEDIUM FOR PRACTICING OF AN INHALATION PROCESS

BACKGROUND OF THE INVENTION

Field of the Invention

This invention relates to an inhalation training system, especially for practicing (in particular, used as synonym for training) of an inhalation process of a patient, a method for practicing of an inhalation process of a patient, a method of using a portable communications device, and an information storage medium.

Description of Related Art

Drugs which are to be inhaled constitute a preferred therapy for patients with asthma, a chronically obstructive pulmonary disease or other chronic or acute conditions or diseases of the respiratory tract.

So-called inhalers are used for inhalation of drugs. The most frequently used inhalers are pressurized metered-dose inhalers (pMDIs) and dry powder inhalers (DPIs). pMDIs were developed to supply a precise amount or dose of a drug in the form of a cloud of aerosol droplets to the lungs of the patient when the latter inhales. Dry powder inhalers are made such that when the patient inhales they supply a metered amount of dry pulverized particles to the lungs.

The effectiveness of drugs which are to be inhaled depends largely on the way the inhaler is used by the patient. Optimally, the correct amount of the drug at the correct instant travels to the desired regions of the lungs. Otherwise, the therapeutic effect is reduced and/or the risk of negative side effects is increased.

The literature contains numerous instances substantiating that many patients incorrectly use inhalers. Instruction of the patient with respect to a correct inhalation technique can improve the use of inhalers. In addition to written and oral instructions, practical exercises are helpful for this purpose.

However, since inhalation generally proceeds subconsciously and develops over the course of a lifetime, it is especially difficult for a patient to change his/her inhalation in order to increase the effectiveness of a drug which is to be inhaled. Rather, it is known that many patients again use suboptimum inhalation even a short time after instruction. Therefore, repeated, preferably regular practicing of inhalation and its checking are recommended.

Inhalation training systems were developed for this purpose. Known inhalation training systems differ from each other with respect to the inhalation model for which the patient is to be trained, with respect to the type of feedback to the patient (for example, acoustically or visually), with respect to the measured variable (for example, inhaled volume, volumetric flow or flow rate or mass flow which is produced during inhalation, velocity of the inhaled particles during the inhalation process), with respect to sensors and actuators (for example, mechanical, magnetic or electronic) and with respect to size, handling and costs. Some inhalation training systems use inhalers which are available on the market, while other inhalation training systems copy or emulate inhalers or parts of them.

U.S. Patent Application Publication No. 2004/0187869 A1 which forms the starting point of this invention shows a dedicated inhalation training system which has a mouthpiece and a converter apparatus. The converter apparatus converts an air flow which occurs in the mouthpiece in a patient inhalation process into a pressure drop or negative pressure. A control circuit converts the pressure drop or negative pressure into an analog, linearized signal.

SUMMARY OF THE INVENTION

The object of this invention is to devise an inhalation training system, a method, a use and an information storage medium, effective, simple, reliable and/or economical practicing of an inhalation process of a patient with electronic feedback to the patient and/or a third party and/or a simple economical and/or durable structure and/or the use of portable communications devices being enabled.

This object is achieved by an inhalation training system, methods and an information storage medium as described herein.

According to one aspect of this invention, the inhalation training system has a holding apparatus which is made to hold an electronic device so that the electronic device can measure or detect the, especially acoustic, signal which has been provided by an, especially only, mechanically operating converter apparatus. The electronic device within the scope of this invention is a device which is preferably separate or independent of the converter apparatus and which need not be connected to the converter apparatus.

The holding device is used for holding the electronic device in a certain desired position, especially detachable holding, therefore without attaching it permanently. Using the holding apparatus in accordance with the invention, an alignment of the electronic device relative to the converter apparatus by the patient is not necessary. The holding apparatus in accordance with the invention preferably enables optimum alignment of the electronic device to the converter apparatus and prevents or reduces displacements of the electronic device out of the desired position. Repeated re-alignment by the patient is not necessary.

Thanks to the holding apparatus in accordance with the invention, the patient need not hold the electronic device itself in one or both hands.

The inhalation training system in accordance with the invention enables effective, comfortable and reliable practicing of an inhalation process. Furthermore, the holding apparatus offers protection of the electronic device, for example, against damage.

The converter apparatus in accordance with the invention is preferably not made for further processing, evaluation and/or feedback of the signal. According to this invention, these steps are preferably carried out only by the electronic device. To do this, the electronic device measures or detects the signal.

The execution of the inhalation training system in accordance with the invention enables a simple, durable and economical structure of the converter apparatus, especially as a whistle, and electronic feedback to the patient and/or a third party.

The inhalation training system in accordance with the invention enables exploitation of the functionality of the electronic device, especially for processing and/or evaluation of the signal and/or for feedback to the patient and/or a third party in a simple, reliable and economical manner.

At the same time, the inhalation training system in accordance with the invention enables expansion of the functionality of the electronic device in a simple and economical manner with respect to practicing of an inhalation process of a patient.

Another aspect of this invention relates to a method for practicing an inhalation process of a patient. According to this aspect, an air flow which occurs in the inhalation process of the patient is converted by a converter apparatus into an acoustic signal and this acoustic signal is electronically evaluated.

The method in accordance with the invention enables the implementation of a simple, durable, reliable and economical converter apparatus. Moreover the method enables effective, simple, reliable and economical practicing of an inhalation process of a patient.

Another aspect of this invention relates to a portable communications device. According to this aspect, the portable communications device is used to practice an inhalation process of a patient.

Portable communications devices for the purposes of this invention are especially electronic devices which are made for detection, input, transmission and/or output of information and which can be easily transported by an individual. The information can be of an acoustic, visual and/or other sensory nature. Typical applications of portable communications devices are telephony, data transmission, games, text processing, table processing, image processing, photography and music reproduction. Typical examples of portable communications devices are mobile phones, smartphones, tablet PCs, handhelds and PDAs.

The use of the portable communications device in accordance with the invention makes it possible to easily and economically expand the functionality of the portable communications device with respect to practicing a patient inhalation process.

At the same time, the use in accordance with the invention enables exploitation of the extensive functionality of typical portable communications devices, especially with respect to processing and evaluation of signals and with respect to the interactive multimedia possibilities for feedback to the patient and/or a third part for practicing of a patient inhalation process.

As a result of the popularity of portable communications devices, access to inhalation training can also be provided to patients who would not like to procure a special device only for inhalation training. Since the owners of portable communications devices are accustomed to their handling, use in accordance with the invention also enables easier and faster learning of an optimum inhalation process. Since many individuals continually carry a portable communications device, the use in accordance with the invention can also lead to more frequent, possibly regular inhalation training.

Furthermore, the use in accordance with the invention increases the ease of operation and the portability of inhalation training.

Another aspect of this invention relates to an information storage medium, especially for a portable communications device. Instructions are stored on the information storage medium in accordance with the invention, and when they are executed by a processor, they preferably cause the following steps to be carried out:
  initialization of a graphic user interface,
  evaluation of a visual start indication,
  read-out of an electrical signal value of an acoustic signal detector,
  digitization and storage of the electrical signal value and
  determination of an effective inhalation time and/or inhaled dose of drug.

The information storage medium in accordance with the invention enables effective, simple, reliable and economical practicing of a patient inhalation process. Moreover, the information storage medium in accordance with the invention allows the method in accordance with the invention and/or the use in accordance with the invention to be implemented effectively, easily and/or economically.

In the following descriptions certain terms used are defined as follows.

The term "inhalation process" in accordance with the invention preferably comprises inhalation of the patient, wherein inhalation can be interrupted over a short time interval, therefore it can comprise inhalation breaths in rapid succession. Furthermore, an inhalation process can also comprise stopping of the air or of the inhalation and/or the exhalation and/or a coughing of the patient.

The term "patient" in accordance with the invention designates preferably an individual who must and/or would like to use an inhaler, especially an individual who is suffering from a disease of the respiratory tract, quite especially from asthma or a chronically obstructive pulmonary disease, and is treating the disease by means of an inhaler.

The term "air flow" for the purposes of this invention is defined preferably as a measurable flowing movement of air with or without turbulence. The term "air flow connection" in accordance with the invention preferably designates a connection of this type for flowing air through which at least one part of an air flow can flow.

These aspects and features of this invention and the aspects and features of the invention which follow from the further description can be implemented independently of one another, but also in any combination.

Other advantages, features, properties and aspects of this invention will become apparent from the following description of preferred embodiments with reference to the accompanying drawings.

DETAILED DESCRIPTION OF THE INVENTION

In the figures, the same reference numbers are used for the same or similar parts, corresponding properties and advantages being achieved even if a repeated description is omitted.

Figure 1:
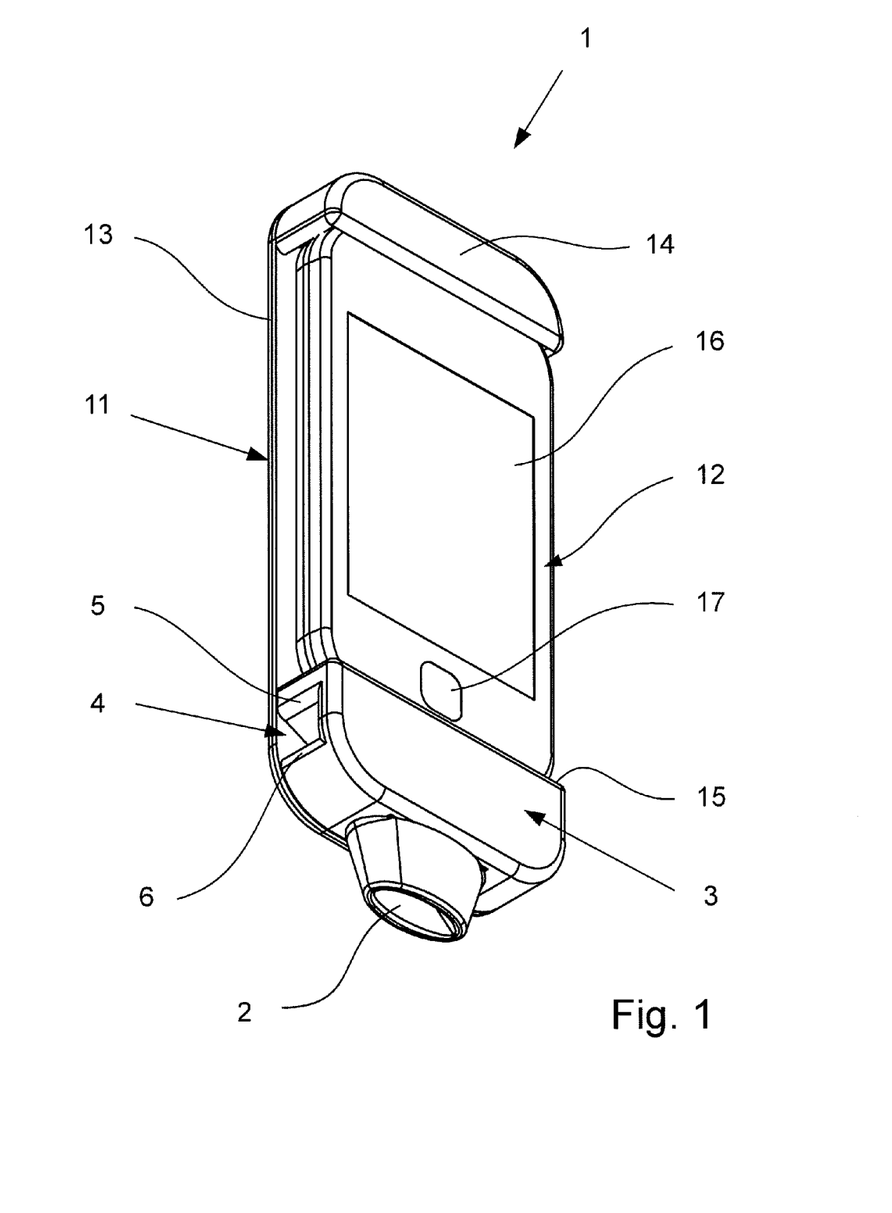
FIG. 1 is a schematic perspective view of a first preferred embodiment of an inhalation training system in accordance with the invention with an electronic device.
Figure 2:
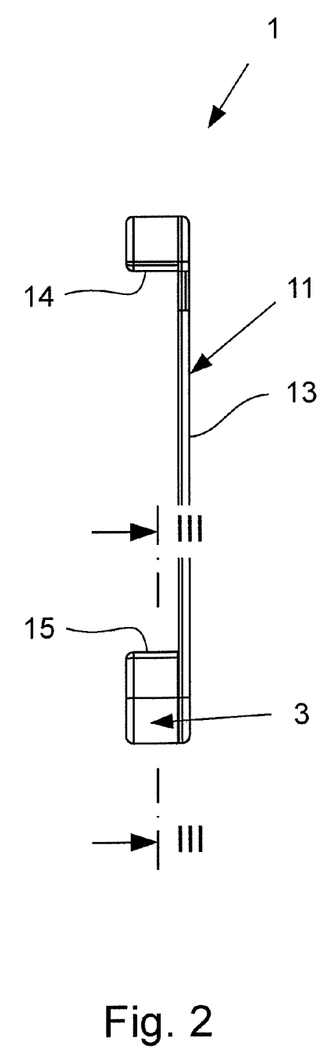
FIG. 2 is a schematic side view of the inhalation training system according to FIG. 1, but without the mouthpiece and without the electronic device.
Figure 3:
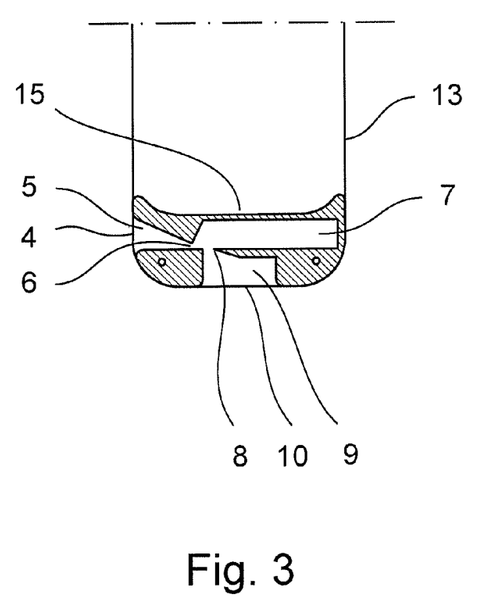
FIG. 3 schematically shows a partial section taken along line in FIG. 2.

FIG. 1 shows a first preferred embodiment of an inhalation training system 1 in accordance with the invention with an electronic device 12. FIG. 2 schematically shows a side view, but without the mouthpiece 2 and without the electronic device 12. FIG. 3 schematically shows a partial section according to line III-III from FIG. 2.

The inhalation training system 1 is used for practicing inhalation by a patient (not shown) and has a mouthpiece 2 and a converter apparatus 3.

Preferably, different types of mouthpieces, especially of dry powder inhalers and/or pressurized metered dosage inhalers, if necessary with or without triggers, can be used as the mouthpiece 2.

Preferably, the mouthpiece 2 is detachably connected to the inhalation training system 1 or the converter apparatus 3 and/or is made interchangeable. In particular, the mouthpiece 2 is plugged or slipped onto the converter apparatus 3. However, the mouthpiece 2 can also be connected or connectable to the converter apparatus 3, for example, by means of a thread, magnet, clip or the like.

The mouthpiece 2 is in an air flow connection to the converter apparatus 3, at least during the inhalation process, so that during inhalation, especially inspiration, air flows or is taken in through the mouthpiece 2 and at least partially also through the converter apparatus 3.

The patient takes the mouthpiece 2 into his/her mouth for use. In an inhalation process, especially during inspiration, air flows through the converter apparatus 3 and the mouthpiece 2, therefore an air flow occurs.

The converter apparatus 3 is made for conversion of the air flow into a signal that is non-optical, and is especially acoustic. To do this, the converter apparatus 3 is preferably made as a whistle. The whistle or converter apparatus 3 is preferably made such that in-taking or inhaling air generates the acoustic signal, and optionally, also exhalation generates the same acoustic signal and/or another acoustic signal (for example, another whistling tone).

First of all, a preferred structure of the converter apparatus 3 is explained in detail below with reference to FIG. 3.

Preferably, the converter apparatus 3 has an air inlet 4, especially one that is laterally located. Proceeding from the air inlet 4, in the illustrated example—especially between two correspondingly shaped walls—a preferably tapered inlet channel 5 is formed which is connected especially via a throttle site 6 to a resonance space 7. Air which is flowing in via the air inlet 4 and which is routed through the inlet channel 5 can flow via a preferably lateral opening which is located especially downstream of the throttle site 6 or in the resonance space 7 into an outlet channel 9. In doing so the air flow is preferably incident obliquely on an edge 8 of the opening so that the air striking the edge 8 causes turbulence on the edge 8, as a result of which standing waves are produced in the resonance space 7. The standing waves generate the acoustic signal or one or more tones which emerge from the converter apparatus 3 via the outlet channel 9 or via a tone outlet 10.

Preferably, the acoustic signal is an audible signal and especially audible whistling.

From the outlet channel 9 or tone outlet 10 the air then flows into the following mouthpiece 2 which is therefore in an air flow connection. This applies during inhalation. During exhalation, the air can flow in reverse and/or optionally can take a different flow path. Furthermore, during exhalation if necessary an acoustic signal may not be produced.

The whistle or converter apparatus 3 is preferably purely mechanical and/or formed only of stationary parts. Preferably, the whistle or converter apparatus 3 is made at least largely of a one-piece construction. Thus, a simple, durable and economical structure of the converter apparatus 3 is enabled.

If necessary, the converter apparatus 3 can also have or can form several whistles. They can respond, for example, depending on an air flow direction and on a volumetric flow or a flow velocity and can produce tones or signals. The tones or signals of the different whistles are then preferably different, for example, with respect to the frequency, spectrum, audibility and/or loudness. In this way, preferably the inhalation and exhalation of the patient can be signaled, and therefore, detected and evaluated accordingly.

Alternatively or in addition, the mouthpiece 2 can also interact with the converter apparatus 3 such that, depending on the respective mouthpiece 2 and its properties (for example, flow resistance), a characteristic acoustic signal (for example, a certain whistling tone) is produced by the converter apparatus 3 in order to signal the mouthpiece 2 or characteristic properties of the mouthpiece 2 in this way, and to enable its detection and evaluation.

The whistles can also be matched to certain types of mouthpieces 2. In particular, the whistles can also be made such that different types of mouthpieces 2 influence a property of the generated whistling such as, for example, the tone level. In this way, the recognition of the respective mouthpiece 2 being used can be accomplished. This information could then be considered in an evaluation of the signal or of the whistling, especially in order to carry out inhalation training more effectively.

The indicated signaling of the respective mouthpiece 2 or of its properties can be enabled, for example, by the converter apparatus 3 or its whistle or signal generation being variable or adjustable or interchangeable, or by the mouthpiece 2 at least partially forming the resonance space 7 and/or some other part of the whistle. Alternatively or in addition, the mouthpiece 2 can also cover or clear one individual whistle or several whistles of the converter apparatus 3 specifically or differently (partially or completely). Alternatively or additionally, the mouthpiece 2 can also form the converter apparatus 3 and/or can be interchangeable together with it.

Preferably, the inhalation training system 1 has a holding apparatus 11 which is made for holding of the electronic device 12 so that the electronic device 12 can measure and detect and especially evaluate the signal which has been made available or has been generated by the converter apparatus 3.

Preferably, the holding apparatus has a rear wall 13, a first or upper holding region 14 and a second or lower holding region 15. The holding regions 14, 15 in the illustrated region each have preferably a recess, depression or the like in order to be able to positively accommodate, hold or encompass the electronic device 12 and/or in particular opposite sides or end regions of the electronic device 12.

The holding regions 14, 15 are preferably movable or adjustable relative to one another in order to be able to accommodate and optionally also again release the electronic device 12. The holding apparatus 11 or rear wall 13 preferably has a telescoping extension 21 (as indicated in the third embodiment in FIGS. 6 and 7) for this purpose so that, for example, the upper holding region 14 can be moved to the lower holding region 15. However, to do this, other designs are also possible. For example, the holding apparatus 11 or the rear wall 13 and/or the holding region 14, 15 can also be made flexible or elastic for this purpose.

To accommodate the electronic device 12, preferably first of all, a lower part of the electronic device 12 is inserted into the lower holding region 15 and the electronic device 12 is leaned or pressed against the rear wall 13. Then, the upper holding region 14 can be pushed down or toward the other holding region 15 by means of the telescoping extension 21 until it holds or encompasses the electronic device 12 also at the top, especially by form-fit.

The holding apparatus 11 or the telescoping extension 21 is preferably made such that (unintentional) release of the electronic device 12 is prevented. For this purpose, there can be a ratchet, sufficient tightness or clamping, a locking means or the like especially with respect to the telescoping extension 21. The holding apparatus 11 is preferably made such that the electronic device 12 can be detached again.

Therefore, in the inserted position the holding apparatus 11 encompasses the electronic device 12 on opposite sides. Here, the electronic device 12 is partially overlapped by the holding apparatus 11. In any case, a screen 16, a control knob or a microphone 17, and optionally, a speaker of the electronic device 12 are not overlapped by the holding apparatus 11 so that for the patient, in particular, the screen 16 is visible and the control knob or the microphone 17, and optionally, the speaker are accessible. In this way, for example, telephoning with the electronic device 12 in the inserted position is enabled.

The holding apparatus 11 can preferably be matched to the shape and/or size of different electronic devices 12.

Preferably, the holding apparatus 11 is made for detachable holding of the electronic device 12. The electronic device 12 can be removed again especially by pushing the upper holding region 14 up.

Alternatively or in addition to the preferred positive or described holding, the holding apparatus 11 can also be executed by means of a magnetic or elastic mechanism for detachable holding of the electronic device 12.

The holding apparatus 11 is preferably made for the positioning or alignment of the electronic device 12 relative to the converter apparatus 3 so that the electronic device 12 or its microphone 17 can in particular optimally and reliably measure the signal.

Preferably, the mouthpiece 2, the converter apparatus 3 and/or the holding apparatus 11 form a unit, especially the holding apparatus 11 and the converter apparatus 3 not being detachable from one another.

Furthermore, the mouthpiece 2, the converter apparatus 3 and/or the holding apparatus 11 are made of plastic and/or have no electronic components.

Further embodiments are explained below using the other figures, but in particular, only important differences being explained so that the statements and explanations so far apply especially additionally or accordingly.

Figure 4:
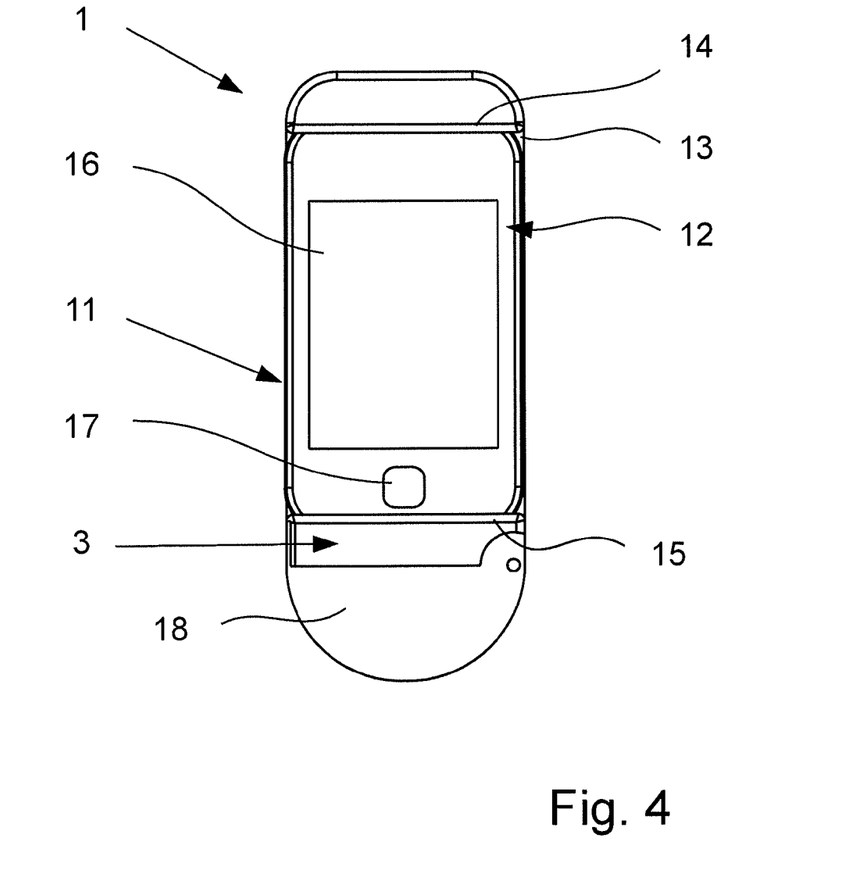
FIG. 4 is schematic a front view of a second preferred embodiment of the inhalation training system in accordance with the invention.

FIG. 4 schematically shows a front view of a second preferred embodiment of the inhalation training system 1 in accordance with the invention. In particular, the inhalation training system 1 has a protective cap 18 which covers the mouthpiece 2 when not in use and which can be detached or pivoted for use, in particular.

Figure 5:
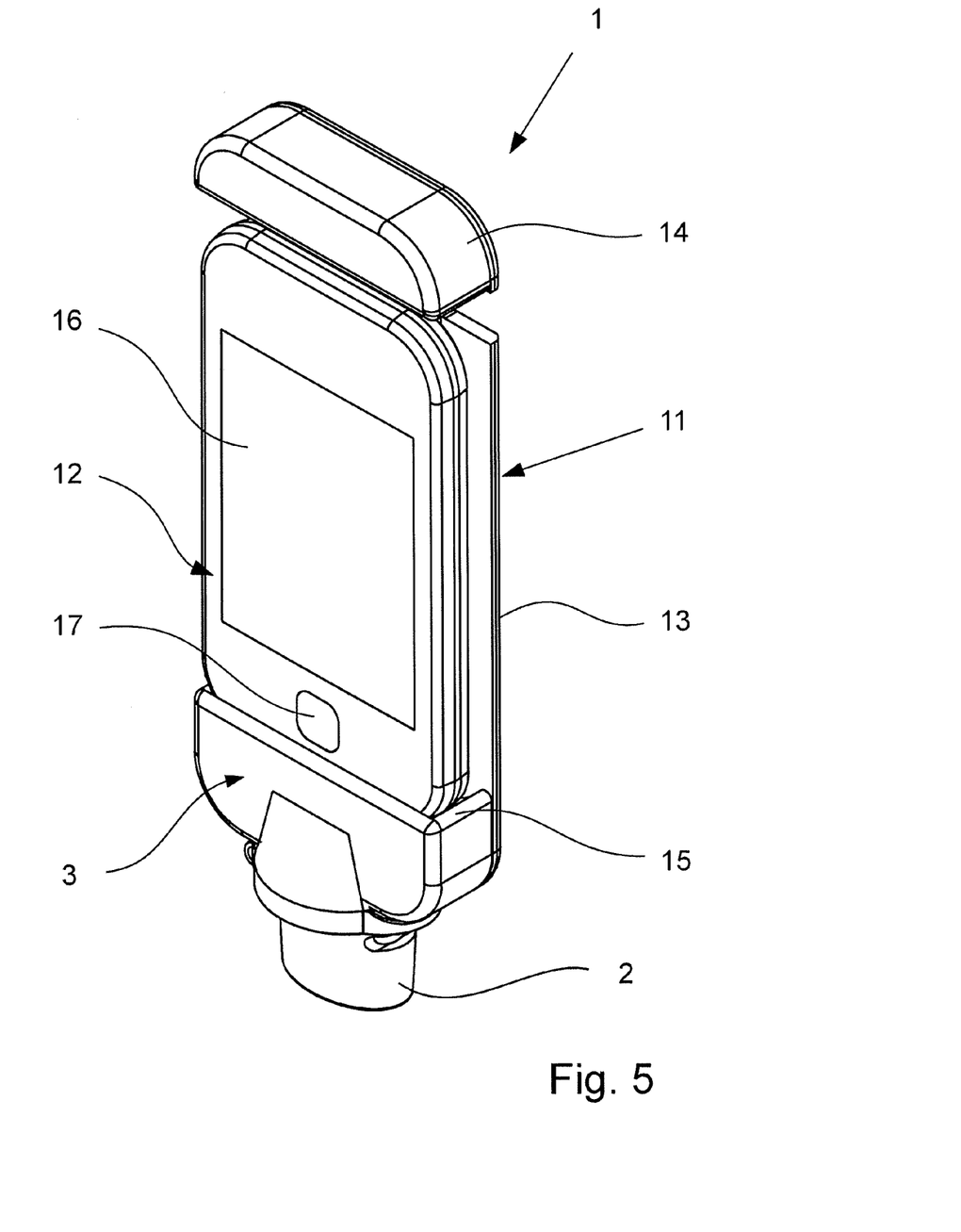
FIG. 5 is a schematic perspective view of a third preferred embodiment of the inhalation training system in accordance with the invention with an electronic device.
Figure 6:
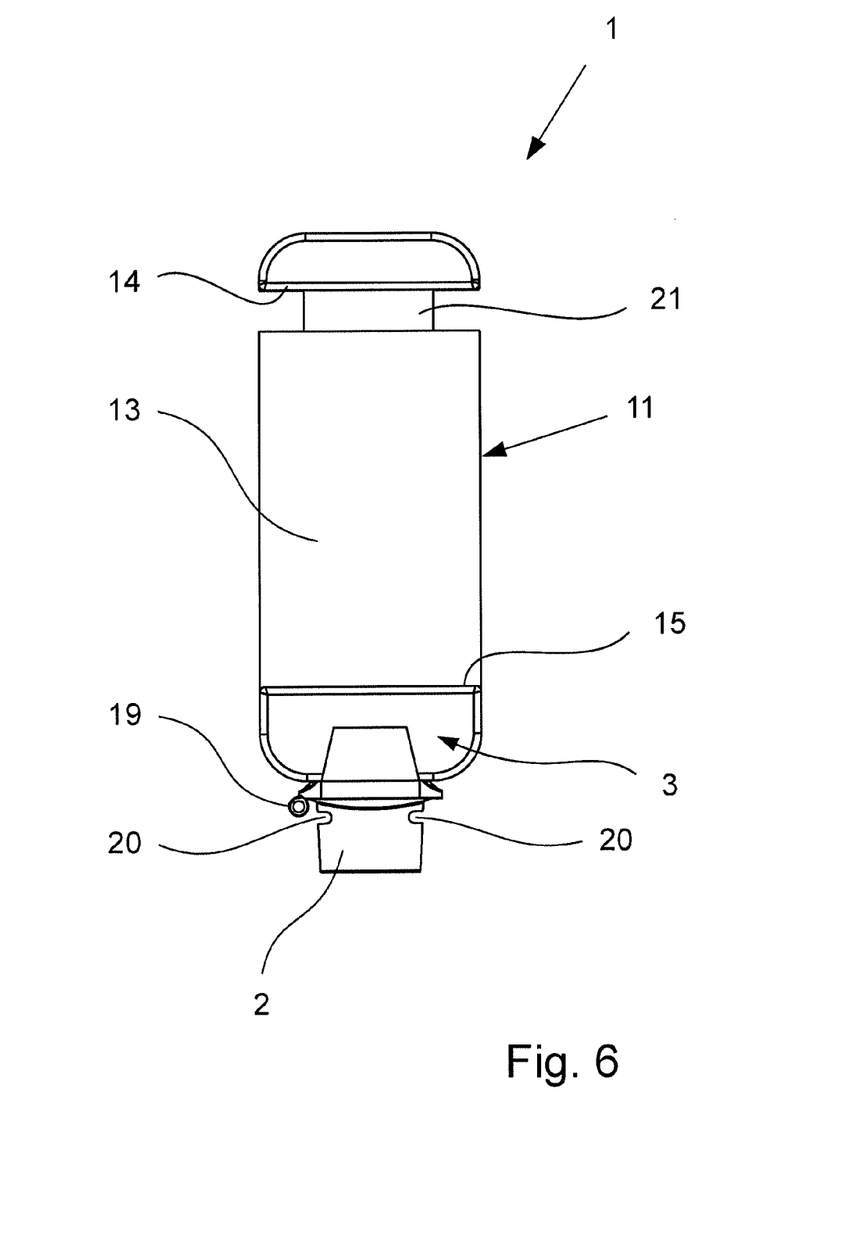
FIG. 6 is a schematic front view of the inhalation training system according to FIG. 5, but without an electronic device.
Figure 7:
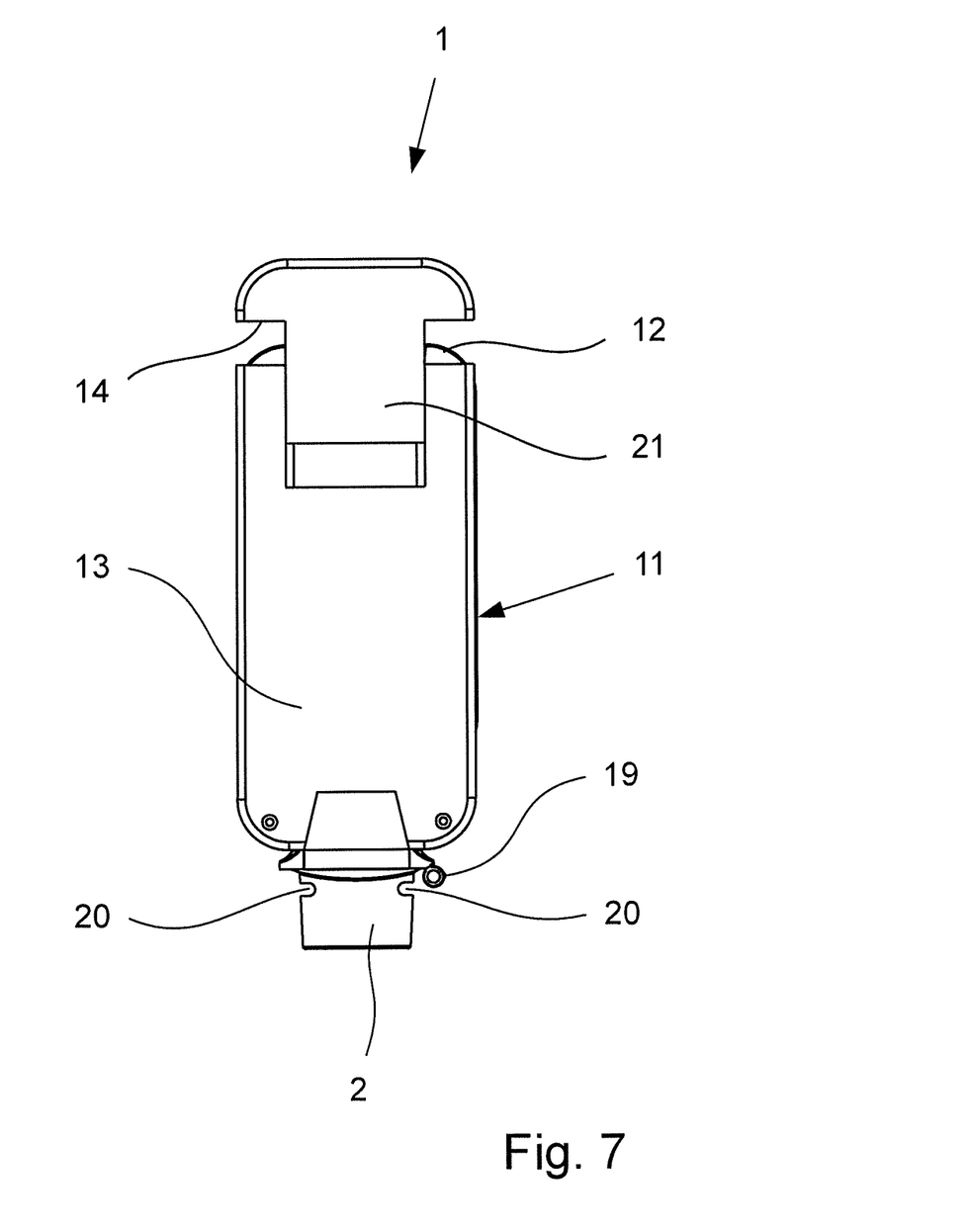
FIG. 7 is a schematic rear view of the inhalation training system according to FIG. 6.

FIGS. 5 to 7 show a third preferred embodiment of the inhalation training system 1 in accordance with the invention. FIG. 5 shows the inhalation training system 1 with the electronic device 12, the upper holding region 14 not yet being slipped onto the device 12. FIG. 6 shows the inhalation training system 1 without the device 12 in a front view. FIG. 7 shows the inhalation training system 1 without the device 12 in a rear view.

In the third embodiment, the inhalation training system 1 is made somewhat differently in the region of the mouthpiece 2. In particular, the mouthpiece 2 or a connected holding section for the patient extends on one or both flat sides laterally over the converter apparatus 3 or the holding apparatus 11.

FIGS. 6 and 7 show an optimum bearing arrangement 19 for a protective cap 18 which can be especially pivoted or locked on. The bearing arrangement 19 is formed, for example, on the mouthpiece 2.

Furthermore, the mouthpiece 2 can have one or more intake air openings 20 through which air can be taken in during inhalation—therefore, past the converter apparatus 3.

Individual aspects and features of the different embodiments and the embodiments themselves can be optionally combined with one another, but can also be implemented independently of one another.

The following statements apply to all embodiments.

The electronic device 12 is especially a portable communications device, such as a telephone, a smartphone or the like.

Preferably, the electronic device 12 is designed to measure the signal which has been made available or produced by the converter apparatus 3, to measure the values of the signal, to process the measured values of the signal and/or to evaluate or process measured values of the signal.

To measure or detect the signal the electronic device 12 receives the signal, preferably with the microphone 17. For processing of the measured values of the signal, the electronic device 12 is made preferably for digitization of the measured values. Preferably, the electronic device 12 has at least one microprocessor and/or a program for signal detection, signal measurement, signal evaluation and/or signal display.

Preferably, the electronic device 12 is designed for determining or estimating the amplitude, frequency and/or phase of the acoustic signal.

Preferably, the electronic device 12 is designed for storage, output and/or especially interactive feedback of measured, processed and/or evaluated signal values to the patient and/or a third party. In particular, the electronic device 12 has a device for acoustic feedback of the evaluation, for example, a speaker, and/or for visual feedback of the evaluation, for example, a screen 16.

The electronic device 12 can, in particular, provide instructions for correct inhalation and/or advice for optimization. For more effective training of the patient, the electronic device 12 can additionally display pictures and/or videos which illustrate an optimum inhalation process.

The term "interactivity" designates the properties of making available to the patient intervention and control possibilities for individualized learning. To do this, for example, the choice and the type of representation of information can be adapted to prior knowledge, the interests and needs of the patient or can be manipulated by him. Solely making available information does not constitute interactive feedback for the purposes of this invention.

Preferably, the electronic device 12 is designed for especially wireless transmission of measured, processed and/or evaluated signal values to another electronic device. In this way, these values can be transmitted, for example, to a physician who can prepare a diagnosis on this basis and/or can give advice for improving the inhalation process.

Preferably, the electronic device 12 is designed for additional applications, especially telephony, data transmission, games, text processing, table processing, image processing, photography or music reproduction. This enhances the utility or usability of the inhalation training system 1 in accordance with the invention.

The inhalation training system 1 can also be made for monitoring of the triggering of the inhalation process. Thus, for example, it can be evaluated whether the inhalation process has been triggered at the correct instant by the patient. This can increase the effectiveness of training.

To do this, for example, the electronic device 12 can be made such that an input of the patient, for example, the actuation of the control knob 17, marks the start of the inhalation process. Alternatively, the inhalation training system 1, especially the mouthpiece 2, can have a trigger as is used, for example, in inhalers. The trigger can be made such that pressing or releasing the trigger generates an acoustic signal. This acoustic signal can be received by the electronic device 12 by means of a microphone 17 and then can be evaluated at the same time by the electronic device 12. Finally, the electronic device 12 can feed back whether the trigger has been pressed and/or released at the correct time and/or whether inhaling has taken place correctly in time for triggering.

The inhalation training system 1 is preferably designed or can be used for practicing an effective inhalation time $T_{in,eff}$ which is as optimum as possible. In this way, the patient is to be enabled to achieve an effective inhalation time as optimum as possible. In an inhaler the effective inhalation time is preferably the time during an inhalation process, especially the time of inspiration, in which the inhaler delivers an amount or dose of a drug. In particular, the effective inhalation time is the portion of time in which the inhalation process and the delivery of the dose of drug overlap.

Based on the effective inhalation time an inhaled dose of drug (iDoD) can be determined. This applies especially when the drug is delivered with a constant rate. The inhaled dose of drug can be given as a percentage of the delivered dose of drug. The effective inhalation time and the inhaled dose of drug are especially indicative with respect to the quality of the inhalation process.

To practice the effective inhalation time, preferably the electronic device 12 is designed for determination of the effective inhalation time. Preferably, the mouthpiece 2 has a trigger (not shown). Alternatively, the trigger can be formed or simulated, for example, by the control knob 17 or by pressing on the screen 16 or actuating a visual trigger display. Actual delivery of a dose of drug need not take place.

To determine the effective inhalation time, the electronic device 12 can determine a delivery time or spray time. The delivery time or spray time is the time during which a delivery of a dose of drug is carried out or simulated. In particular, the delivery time or spray time can be defined as the time which passes between an actuation of the trigger for starting an (actual or simulated) delivery of a dose of drug and the end of delivery. The end of delivery is preferably fixed by a fixed delivery duration or spray duration (SDur) or by a second, later actuation of the trigger. Preferably, the effective inhalation time is given in a percentage of the spray duration.

In one preferred embodiment, the effective inhalation time is 0% when the delivery time is outside the time of the inhalation process or of inhalation ($T_{in}$), i.e., when the sole or first actuation of the trigger takes place after the end of the inhalation process or when the delivery time has passed before the start of the inhalation process. In this embodiment, the effective inhalation time is 100% when the delivery time is completely within the time of the inhalation process, i.e., when the sole or first actuation of the trigger takes place after the start of the inhalation process and the delivery time has passed before the end of the inhalation process.

If the delivery begins before the start of the inhalation process and the delivery ends after the end of the inhalation process, the effective inhalation time is determined preferably according to the following formula:

$$T_{in,eff}[\%] = \frac{T_{in} \cdot 100}{SDur}.$$

If the delivery starts after the start and before the end of the inhalation process and the delivery ends after the end of the inhalation process, the effective inhalation process is preferably determined according to the following formula:

$$T_{in,eff}[\%] = \left(1 - \frac{\Delta + SDur - T_{in}}{SDur}\right) \cdot 100,$$

$\Delta$ being the difference between the start of the delivery and start of the inhalation process, i.e., $\Delta$ has a positive value when the delivery starts after the start of the inhalation process and $\Delta$ is a negative value when the delivery starts before the start of the inhalation process.

If the delivery starts before the beginning of the inhalation process and the delivery ends after the start and before the end of the inhalation process, the effective inhalation process is preferably determined according to the following formula:

$$T_{in,eff}[\%] = \left(\frac{\Delta + SDur}{SDur}\right) \cdot 100,$$

$\Delta$ being the difference between the start of the delivery and start of the inhalation process.

In particular, when determining the effective inhalation time, solely the inspiration times can be considered as the inhalation time $T_{in}$. Therefore, if inspiration is interrupted by holding the breath or expiration, these times are preferably subtracted from the inhalation time.

Alternatively or in addition, the electronic device 12 can be designed for determination or estimation of a volumetric flow or flow rate which has been generated in the inhalation process and/or a flow velocity generated here. These two physical quantities are highly indicative with respect to the quality of the inhalation process.

Preferably, the mouthpiece 2, the converter apparatus 3, the holding apparatus 11 and/or the rear wall 13 have at least one surface for attachment of advertising or instructions for use.

Altogether, the inhalation training system 1 easily enables a subsequent improvement of the inhalation process, the lung function and/or the quality of life of the patient.

In the method in accordance with the invention, an air flow which occurs in the inhalation process of the patient is converted by the converter apparatus 3 preferably into audible whistling as an acoustic signal and this audible whistling is electronically evaluated. Preferably, the whistling is detected or measured by an electronic device 12, especially a communications device or a telephone. Preferably, the electronic device 12 picks up the whistling using a microphone or other suitable sensor. For example, the converter apparatus 3 could alternatively or additionally make available an optical signal which is being detected by a camera of the electronic device 12.

Using the recorded signals, preferably the effective inhalation time $T_{in,eff}$ and/or the inhaled dose of drug iDoD are determined by the electronic device 12 as described above. Alternatively or in addition, the electronic device 12 can estimate a volumetric flow which has been generated in the inhalation process and/or a flow velocity which has been generated here. The electronic device 12 therefore also performs electronic evaluation of the signal.

Preferably, acoustic and/or visual notices for correct inhalation and/or for optimization of the inhalation process are provided as feedback to the patient and/or a third party in an especially interactive manner. This configuration increases the effectiveness of training.

Preferably, the method or practicing of inhalation is carried out with software which is matched to the device 12 or communication device and can be ordered, in particular, via an online portal and installed. Typically, this software is called an "App". The use of an App improves the flexibility and ease of operation. The term "App" is also preferably defined as a preferred communications sequence or a preferred method.

The App can be used, for example, for processing and interpretation of the measured signal and for feedback to the patient and/or a third party. To do this the App can be made available or executed using an information storage medium in accordance with the invention. The information storage medium is preferably made for use in a portable communications device, especially optimized with respect to the space requirement, energy consumption, reliability and data transmission rate.

Figure 8:
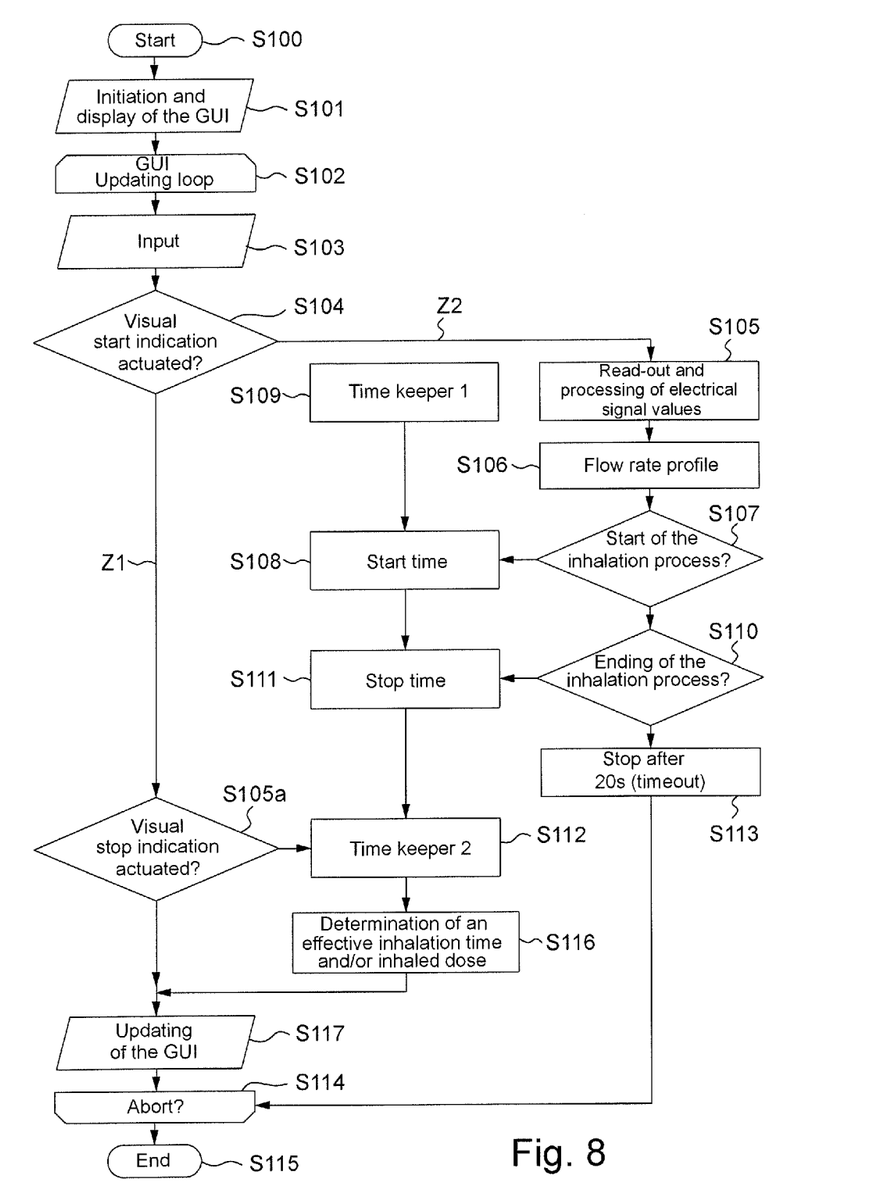
FIG. 8 is a flow chart of a preferred sequence, or an App, which can be executed especially using an information storage medium in accordance with the invention.

Instructions are preferably stored on the information storage medium and when executed by a processor cause the execution of the steps which are described below and which are shown schematically in a flow chart in FIG. 8. FIG. 8 also constitutes a preferred method sequence.

Other steps can be added to the preferred method sequence shown in FIG. 8 or to the described steps of the App. Individual steps of the preferred sequence or the App can also be omitted. The sequence of the individual steps can be changed and different steps can be combined with one another.

In the preferred method sequence which is shown in FIG. 8 or the steps of the App, the App or the portable communications device 12 is started in a first step S100.

In a later step S101, a graphic user interface (GUI) is initiated and preferably displayed on the screen 16 of the portable communications device 12. In particular, a visual start indication or visual trigger indication is also displayed.

In another step S102, a loop function is started using which the GUI is updated in order to display, for example, altered contents of the GUI.

Preferably, the start indication or trigger indication is evaluated using the App or the portable communications device 12. In particular, in a step S103, an input of the user or patient, quite especially the actuation of the start indication or of the trigger indication by the user or patient, is monitored.

The monitoring of the input leads, preferably, to a decision whether the start indication or trigger indication has been actuated, as is indicated in step S104.

If it is decided in step S104 that an actuation of the start indication or trigger indication has taken place, preferably two parallel branches are followed by the App or the method. On the one hand, in a first branch Z1 it is preferably monitored whether a visual stop indication (especially on the screen 16) is actuated. This monitoring leads preferably to a decision whether the stop indication has been actuated, as is indicated in step S105*a*.

On the other hand, in a second branch Z2 parallel to the monitoring of the stop indication in a step S105 an electrical signal value or several electrical signal values of an acoustic signal detector, for example, of a microphone of the portable communications device 12, is or are read out. An electrical signal value of the acoustic signal detector can be obtained, for example, by the method in accordance with the invention. Preferably, the App or the portable communications device 12 in step S105 induces processing of the electrical signal values, especially digitization and storage of the electrical signal values.

In another step S106, in the branch Z2 a volumetric flow or flow rate which has been produced in the inhalation process is determined and/or a flow rate profile is prepared using the App or the portable communications device 12.

Within the branch Z2, preferably, the starting of an inhalation process is monitored by the App or the portable communications device 12. Monitoring leads preferably to a decision whether the inhalation process has been started, as is indicated in step S107.

Here, the App or the portable communications device 12 is preferably designed such that an actuation of the trigger is interpreted as the starting of an inhalation process; this leads to the decision that the inhalation process has started. Actuation of the trigger can produce, for example, an acoustic signal. This acoustic signal can be picked up by means of the acoustic signal detector and then can be evaluated by the App or the portable communications device 12.

Alternatively, the App or the portable communications device 12 can also be designed such that an actuation of the trigger indication is interpreted as starting of an inhalation process.

If it is decided in step S107 that an inhalation process has started, on the one hand, in a step S108, preferably a starting time is determined by the App or the portable communications device 12. In addition, preferably still further time values can be determined by the App or the portable communications device 12 via time keepers, for example, in a step S109.

If it is decided, in step S107, that an inhalation process has started, on the other hand preferably the ending of the inhalation process is monitored by the App or the portable communications device 12. The monitoring leads preferably to a decision whether the inhalation process has ended, as is indicated in step S110.

Here, the App or the portable communications device 12 is preferably designed such that release of the trigger is interpreted as ending of the inhalation process; this leads to the decision that the inhalation process has ended. Release of the trigger can, for example, generate an acoustic signal. This acoustic signal can be picked up by means of the acoustic signal detector and then can be evaluated by the App or the portable communications device 12.

Alternatively, the App or the portable communications device 12 can also be designed such that a repeated actuation of the trigger indication or an actuation of the ending indication (especially on the screen 16) is interpreted as ending of the inhalation process.

If it is decided in step S110 that the inhalation process has ended, in a step S111 preferably a stop time is determined by the App or the portable communications device 12.

If the monitoring of the ending of the inhalation process, after passage of a defined time (for example, 20 seconds)

beginning from a fixed start of the inhalation process does not lead to a decision that the inhalation process has ended, preferably ending or abort of the App or the sequence takes place. Preferably, an abort is checked in step S114. If an abort is ascertained by the App or the portable communications device 12, the App or the sequence is ended in a step S115.

In step S115, for example, the GUI can be ended so that it is no longer displayed. Furthermore, in step S115, time values can be reset and/or memories can be released.

In step S111 if a stop time is determined, in the preferred method sequence in FIG. 8, a time keeper is preferably determined by the App or the portable communications device 12 in a step S112. Moreover, preferably an evaluation of the electrical signal values is undertaken. Thus, in a step S116, for example, using the App or the portable communications device 12, an effective inhalation time and/or inhaled dose of drug can be determined, as already described.

Results of the evaluation can be displayed on the graphic user interface or the screen 16, for which the graphic user interface can be updated in a step S117.

Furthermore, the App or the portable communications device 12 is preferably made such that feedback to the patient and/or a third party takes place, especially an alarm indication is output, when the flow rate which has been determined by the App or the portable communications device 12 rises above a value of roughly 40 liters per minute and/or drops below a value of roughly 20 liters per minute.

If it is decided in step S105a that the stop indication has been actuated, preferably the GUI is updated in step S117 and/or an abort is checked in step S114.

The App or the training process can also be ended or aborted by actuating an abort indication (especially on the screen 16).

Individual steps of the App can also be implemented independently of other steps.

What is claimed is:

1. An inhalation training system for practicing of an inhalation process of a patient without a capability for dispensing of an inhalant, comprising:
   a body portion without a means for receiving a through-flow of air or inhalant,
   a mouthpiece for enabling an air flow to be produced upon inhalation by a patient thereat, said mouthpiece being connected to an end of the body portion,
   a converter apparatus that has a whistle, the whistle being located at the mouthpiece in a manner able to produce an audible whistling from the air flow, and
   a portable communications device that is adapted to receive the whistling by means of a microphone and which is detachably located within said body portion,
   wherein the portable communications device is one of a mobile phone and a tablet computer,
   wherein the body portion comprises a holding apparatus having an interior space sized for receiving and holding the portable communications device in a position for measuring the signal produced by the converter apparatus, and
   wherein the holding apparatus is constructed for detachable holding of the portable communications device.

2. The inhalation training system as claimed in claim 1, wherein the holding apparatus is adapted to at least partially encompass the portable communications device on opposite sides thereof.

3. The inhalation training system as claimed in claim 1, wherein the converter apparatus is adapted to produce a characteristic acoustic signal indicative of a type of the mouthpiece and to enable detection and evaluation thereof.

4. The inhalation training system as claimed in claim 1, wherein the holding apparatus comprises two holding regions, which are movable relative to one another in order to open the interior space to enable insertion and removal of the portable communications device into and from the body portion.

5. The inhalation training system as claimed in claim 1, wherein the portable communications device is mechanically connected to the converter apparatus, when the portable communications device is held by the holding apparatus.

* * * * *